United States Patent
Harsar et al.

(10) Patent No.: US 11,988,899 B2
(45) Date of Patent: May 21, 2024

(54) PROTECTIVE SHIELD AND EYEWEAR INCORPORATING SAME

(71) Applicants: Michael Harsar, Avon, OH (US); Albert S. Harsar, Avon, OH (US)

(72) Inventors: Michael Harsar, Avon, OH (US); Albert S. Harsar, Avon, OH (US)

( * ) Notice: Subject to any disclaimer, the term of this patent is extended or adjusted under 35 U.S.C. 154(b) by 109 days.

(21) Appl. No.: 17/576,885

(22) Filed: Jan. 14, 2022

(65) Prior Publication Data
US 2022/0218052 A1    Jul. 14, 2022

Related U.S. Application Data

(60) Provisional application No. 63/137,217, filed on Jan. 14, 2021.

(51) Int. Cl.
| | | |
|---|---|---|
| *G02C 11/00* | (2006.01) | |
| *A61F 9/04* | (2006.01) | |
| *G02C 7/16* | (2006.01) | |
| *G02C 9/04* | (2006.01) | |

(52) U.S. Cl.
CPC .............. *G02C 11/12* (2013.01); *A61F 9/045* (2013.01); *G02C 9/04* (2013.01); *G02C 7/16* (2013.01)

(58) Field of Classification Search
CPC .. G02C 11/12; G02C 9/04; G02C 7/16; A61F 9/045
USPC .................................................. 2/13; 351/155
See application file for complete search history.

(56) References Cited

U.S. PATENT DOCUMENTS

| | | | | |
|---|---|---|---|---|
| 485,448 | A * | 11/1892 | Beilmann ................ | G02C 7/16 2/13 |
| 546,636 | A * | 9/1895 | Brandly ................... | G02C 7/16 2/13 |
| 886,209 | A * | 4/1908 | Henry ...................... | G02C 7/16 2/13 |
| 932,703 | A * | 8/1909 | Henry ...................... | G02C 7/16 2/13 |
| 1,585,023 | A * | 5/1926 | Fant ......................... | G02C 7/16 2/13 |
| 1,834,415 | A * | 12/1931 | O'Meara ................. | G02C 11/00 2/13 |
| 2,342,377 | A * | 2/1944 | Small ...................... | G02C 11/12 2/13 |
| 2,620,472 | A * | 12/1952 | Abrahamson ........... | G02C 7/16 2/13 |
| 2,640,195 | A * | 6/1953 | Bricker .................... | G02C 7/16 2/13 |

(Continued)

FOREIGN PATENT DOCUMENTS

| | | | | |
|---|---|---|---|---|
| EP | 1020753 | A1 * | 7/2000 | ............. G02C 11/00 |
| GB | 191300693 | A * | 12/1913 | ............... G02C 7/16 |

(Continued)

*Primary Examiner* — George G. King
(74) *Attorney, Agent, or Firm* — Curatolo Sidoti & Trillis Co., LPA; Salvatore A. Sidoti; Floyd Trillis, III

(57) ABSTRACT

A protective shield for eyewear includes a body having opposite facing top and bottom major surfaces and a perimeter. The perimeter is defined by front, rear, and side regions. The rear region of the body is configured to have a concave surface to conform to the surface of a wearer's forehead. The bottom surface of the body includes one or more attachment members configured to permit the removable attachment of the body to eyewear.

12 Claims, 7 Drawing Sheets

(56) References Cited

U.S. PATENT DOCUMENTS

| | | | | |
|---|---|---|---|---|
| 2,691,165 A | * | 10/1954 | Kane | G02C 7/16 2/13 |
| 2,708,269 A | * | 5/1955 | Von Gunten | G02C 7/16 2/13 |
| 2,752,598 A | * | 7/1956 | Abels | G02C 7/16 2/13 |
| 3,011,170 A | * | 12/1961 | Lutz | G02C 7/16 2/13 |
| 5,335,025 A | * | 8/1994 | Wang | G02C 7/16 351/44 |
| 5,712,697 A | * | 1/1998 | Walton | G02C 9/00 351/44 |
| 2012/0075570 A1 | * | 3/2012 | Tubin | G02C 3/02 351/44 |

FOREIGN PATENT DOCUMENTS

| | | | | | |
|---|---|---|---|---|---|
| GB | 266498 A | * | 3/1927 | | G02C 7/16 |
| GB | 315113 A | * | 7/1929 | | G02C 7/16 |
| GB | 467299 | * | 6/1937 | | G02C 9/04 |
| KR | 20130019690 | * | 2/2013 | | G02C 7/16 |

* cited by examiner

PROTECTIVE SHIELD AND EYEWEAR INCORPORATING SAME

CROSS REFERENCE TO RELATED APPLICATIONS

This application claims the benefit of the filing date under 35 U.S.C. § 119(e) of United States Provisional Application for Patent Ser. No. 63/137,217 filed on Jan. 14, 2021, which is incorporated herein by reference.

TECHNICAL FIELD

The present disclosure relates to a protective shield configured to be removably attached to eyewear for shielding wearer's eyes from bright light from the sun or other light sources and debris, and eyewear incorporating the protective shield.

BACKGROUND

Conventional eyewear frames, while functional for their protective or vision correction purposes, are not completely satisfactory in all situations. For example, overhead glare and bright light from the sun and other sources can enter the space between the eyeglasses and the wearer's face, and contact the eyes without passing through the eyeglass lenses. Therefore, people often wear a hat with their eyewear to reduce their exposure to sun glare or bright lights.

It is desirable to provide a protective shield which can be expeditiously attached and detached from eyewear of any type and to provide partial or complete blockage of sun glare and bright light. The protective shield is also useful for preventing rain, snow, sleet, etc. from entering the space between the eyewear frame and the wearer's forehead.

SUMMARY

Provided is a protective shield for eyewear comprising a body having opposite facing top and bottom major surfaces, a perimeter, a concave side surface to substantially conform to a wearer's forehead, one or more attachment members depending from the bottom surface of the body and configured to removably attach the body to eyewear.

Additionally provided is a combination comprising eyewear having a frame and a protective shield removably attached to the eyewear, the protective shield comprising a body having opposite facing top and bottom major surfaces, a perimeter, a concave side surface to substantially conform to a wearer's forehead, one or more attachment members depending from the bottom surface of the body and configured to removably attach the body to eyewear.

BRIEF DESCRIPTION OF THE DRAWINGS

The present disclosure will be more readily understood from the detailed description of illustrative embodiments presented below considered in conjunction with the attached drawings, of which.

Figure 1:
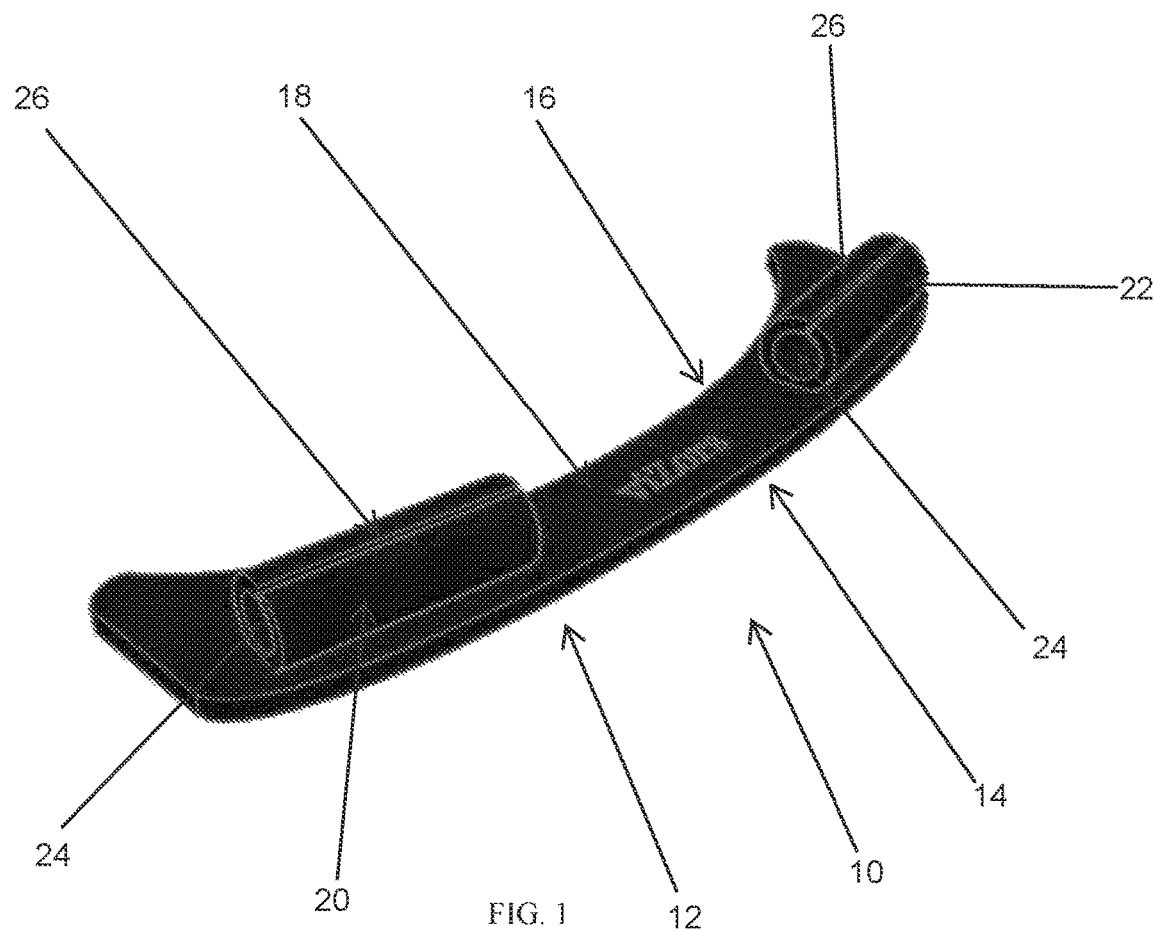
FIG. 1 is a bottom perspective view of one illustrative embodiment of the protective shield.

It is to be understood that the attached drawings are for purposes of illustrating the concepts of the disclosure and may not be to scale, and are not intended to be limiting in terms of the range of possible shapes and/or proportions.

DETAILED DESCRIPTION

Disclosed is a protective barrier or shield that is configured to be attached to eyewear, such as prescription eyeglasses, over-the-counter eyeglasses and sunglasses. The protective shielding comprises a body having opposite facing top and bottom major surfaces, a perimeter, a concave side surface to substantially conform to a wearer's forehead. At least one attachment member depends or otherwise extends from the bottom major surface of the body and is configured to removably attach the body to the eyewear.

The protective shielding comprises a substantially flat or planar body having opposite facing top and bottom major surfaces, a perimeter, a concave side surface to substantially conform to a wearer's forehead. At least one attachment member depends or otherwise extends from the bottom major surface of the body and is configured to removably attach the body to the eyewear.

The protective shielding comprises an opaque or substantially opaque body having opposite facing top and bottom major surfaces, a perimeter, a concave side surface to substantially conform to a wearer's forehead. At least one attachment member depends or otherwise extends from the bottom major surface of the body and is configured to removably attach the body to the eyewear.

The protective shielding comprises a substantially planar and substantially opaque body having opposite facing top and bottom major surfaces, a perimeter, a concave side surface to substantially conform to a wearer's forehead. At least one attachment member depends or otherwise extends from the bottom major surface of the body and is configured to removably attach the body to the eyewear.

The protective shield comprises a body having opposite facing top and bottom major surfaces, a perimeter, a concave side surface to substantially conform to a wearer's forehead. At least one attachment member depends or otherwise extends from the bottom major surface of the body and is configured to removably attach the body to the eyewear, wherein the at least one attachment member is configured and positioned on the body such that when the protective shield is attached to a top portion of eyewear the front edge of the body of the protective shield extends forwardly beyond the eyewear and rearwardly to contact the wearer's forehead.

The protective shield comprises a substantially flat or planer body having opposite facing top and bottom major surfaces, a perimeter, a concave side surface to substantially conform to a wearer's forehead. At least one attachment member depends or otherwise extends from the bottom major surface of the body and is configured to removably attach the body to the eyewear, wherein the at least one attachment member is configured and positioned on the body such that when the protective shield is attached to a top portion of eyewear the front edge of the body of the protective shield extends forwardly beyond the eyewear and rearwardly to contact the wearer's forehead.

The protective shield comprises an opaque or substantially opaque body having opposite facing top and bottom major surfaces, a perimeter, a concave side surface to substantially conform to a wearer's forehead. At least one attachment member depends or otherwise extends from the bottom major surface of the body and is configured to removably attach the body to the eyewear, wherein the at least one attachment member is configured and positioned on the body such that when the protective shield is attached to a top portion of eyewear the front edge of the body of the protective shield extends forwardly beyond the eyewear and rearwardly to contact the wearer's forehead.

When the protective shield is coupled with the eyewear, the body of the protective shield partially or completely blocks glare or bright light from the sun or other light sources from entering the space between the eyewear frame and the wearer's forehead. The body of the protective shield is also configured to partially or completely block rain, sleet, or snow from entering the space between the eyewear frame and the wearer's forehead. The body of the protective shield is also configured to partially or completely block debris an small objects from entering the space between the eyewear frame and the wearer's forehead. Another advantage of the protective shield is that it is configured to be removed from the eyewear without requiring removal of the eyewear from the user's head.

According to certain embodiments, the body of the protective shield is provides a protective overhang for the lenses of any type of eyewear. The body of the protective shield is shaped and configured to provide a physical overhang and protection to the lenses of the eyewear, while conforming to the general shape of the user's forehead to provide more complete protection from the elements.

According to an illustrative embodiment, the body of the protective shield may be substantially crescent-shaped with rounded opposite ends to conform to the surface of the forehead of the wearer. It should be noted, however, that the body of the protective shield may be configured in other shapes.

The body of the protective shield may be composed of any suitable resilient material. According to certain embodiments, the protective shield may be made from a variety of polymer materials. For example, and not in limitation, the body of the protective shield may be made from elastomeric materials or hard plastics.

According to certain embodiments, at least a portion of the body of the protective shield may be composed of a water-resilient or waterproof material.

According to certain embodiments, at least a portion of the body of the protective shield may be flexible. The protective shield may be manufactured using an injection molding process, an extrusion process, a vacuum forming process, a slushing molding process, a casting process, a spray forming process, a compression molding process, a 3D printing process, or other processes known in the art. Advantageously, the protective shield may be manufactured in a relatively simple and efficient manner with reduced manufacturing and material costs.

According to certain embodiments, the protective shield is made of a relatively soft and pliable material such as vinyl, Santoprene®, a thermoplastic olefin (TPO), a plastisol, etc. According to certain embodiments, the protective shield is formed from an elastomer resin, including but not limited to, silicone resins, epoxy resins and polyurethane resins. These may be thermoset or thermoplastic resins.

The protective shield can be formed from a soft resin applied to molding by a material extrusion type three-dimensional printer, a resin made of a urethane-based thermoplastic elastomer (for example, "NINJAFLEX (registered trademark)" manufactured by Fenner Drives Corp, USA). Additional suitable thermoplastic materials include: polylactic acid (PLA), acrylonitrile butadiene styrene (ABS), polyether ether ketone (PEEK), polyaryletherketone (PAEK), polytetrafluoroethylene (PTFE), Nylon, or any other suitable thermoplastic material.

According to certain embodiments, the body of the protective shield includes at least one attachment member to removably attach the protective shield to eyewear. According to certain embodiments, the body of the protective shield includes at least two attachment members to removably attach the protective shield to eyewear. The attachment members are configured to fasten, couple, or attach the body of the protective shield to a top portion of eyewear. According to certain embodiments, the attachment members are configured to fasten, couple, or attach the body of the protective shield to a top portion of the frame of eyewear. According to certain embodiments, the one or more attachment members are configured to permit the body to be removably mountable to a central bridge portion of the eyewear. According to certain embodiments, the one or more attachment members do not attach the body to the arms (i.e., the portion on the respective sides of a frame of the eyewear that extends from a hinge and over the ears of a wearer of the eyewear) of a pair of eyeglasses.

The at least one attachment member may be any suitable device configured to attach, clip, or couple to the eyewear in an easy-to-use manner such that the eyewear does not need to be removed in order to attach the protective shield to the eyewear. According to certain embodiments, the one or more attachment members comprise clips, clasps, clamps, friction-fit members, magnets, snaps, or combinations thereof.

According to certain embodiments, the one or more attachment members each comprise a body that depends from the bottom surface of the body. The attachment member may be provided in the form of a block, cube, cuboids, cylinder, rectangular prism, sphere, hemisphere, tube and the like. Any one of these attachment member shapes may be provided as a hollow or solid shape. According to certain embodiments, the attachment member is provided in the form of a cylinder. According to certain embodiments, the protective shield comprises two spaced apart cylindrical attachment members depending from the bottom surface of the body of the protective shield.

The attachment member body includes means for engaging the protective shield to the eyewear formed in a portion of the body of the protective shield. Without limitation and only by way of example, the means for engaging the protective shield to the eyewear may be selected from cuts, canals, channels, depressions, furrows, grooves, openings, ruts, slices, slits, or trenches. Each of these means are configured to attach to a portion of the eyewear in a friction-fit manner. According to certain embodiments, the attachment means is provided in an elongated cylindrical shape and the means for engaging the protective shield to eyewear comprises a slit formed along the longitudinal axis of at least a portion of the length of the cylindrical shape. According to other embodiments, the attachment means is provided in an elongated and hollow cylindrical shape and the means for engaging the protective shield to eyewear comprises a slit formed along the longitudinal axis of at least a portion of the length of the cylindrical shape. According to other embodiments, the attachment means is provided in an elongated and hollow cylindrical shape and the means for engaging the protective shield to eyewear comprises a slit formed along the longitudinal axis the entire length of the cylindrical shape. The slit is configured to be friction-fit over a top portion of a pair of eyeglasses.

The perimeter of the body of the protective shield is defined by a front edge region, a rear edge region, and side edge regions located at opposite longitudinal ends of the body. According to certain embodiments, the one or more attachment members are positioned on the bottom of the body intermediate the front and the rear thereof. According to certain embodiments, the one or more attachment members are positioned on the bottom of the body closer to front edge thereof. According to certain embodiments, the one or more attachment members are positioned on the bottom of the body intermediate closer to the rear edge thereof. According to certain embodiments, the one or more attachment members are integral to the body of the protective shield. According to certain embodiments, the one or more attachment members are removably attached to the body of the protective shield.

FIG. 1 illustrates a bottom perspective view of the protective shield (10), according to embodiments of the present disclosure. As illustrated, the protective shield (10) includes a body (12) including a front edge region (14), a rear edge region (16), a bottom major surface (18) and a top major surface (not shown). In the example, shown, the body (12) is substantially crescent-shaped and is configured for attachment to eyewear (not shown) such that a portion of the body (12) provides a protective shield (10) to the eyes of the wearer. The bottom surface (18) of the body (12) includes first (20) and second (22) attachment members for attaching to a top portion of the eyewear (not shown). First (20) and second 22 attachment members extend from bottom surface (18) of body (12) intermediate the front (14) and the rear (16) portions thereof. First (20) and second (22) attachment members comprise a hollow cylindrical body (24) with first and second ends that define a longitudinal axis, wherein a slit (26) is positioned along a longitudinal portion of the periphery of the first (20) and second (22) attachment members and is configured to receive a top portion of the eyewear (not shown). FIG. 1 shows the first (20) and second (22) attachment members in the closed position. It is noted that any suitable type of attachment member may be used to secure the protective shield (10) to the eyewear, in a manner that can be easily clipped on or off by transitioning the first (20) and second (22) attachment members between the closed and open positions. Advantageously, the protective shield (10) may be positioned to securely and easily clip to at least a top surface of eyewear (not shown) thereby achieving protection for the lenses and the eyes of the wearer from external elements such as rain, sleet, hail, snow, and sun. Another advantage is achieved in that the protective shield (10) may be attached to any type, size, and shape eyewear by having first (20) and second (22) attachment members that can be securely fastened, attached, or coupled to at least a top surface of eyewear without requiring removal of the eyewear from the user's head. An advantage of the embodiments of the present disclosure is achieved in the easy-to-use and universal (e.g., one size fits all) nature of the first (20) and second (22) attachment members as it relates to a variety of eyewear.

Figure 2:
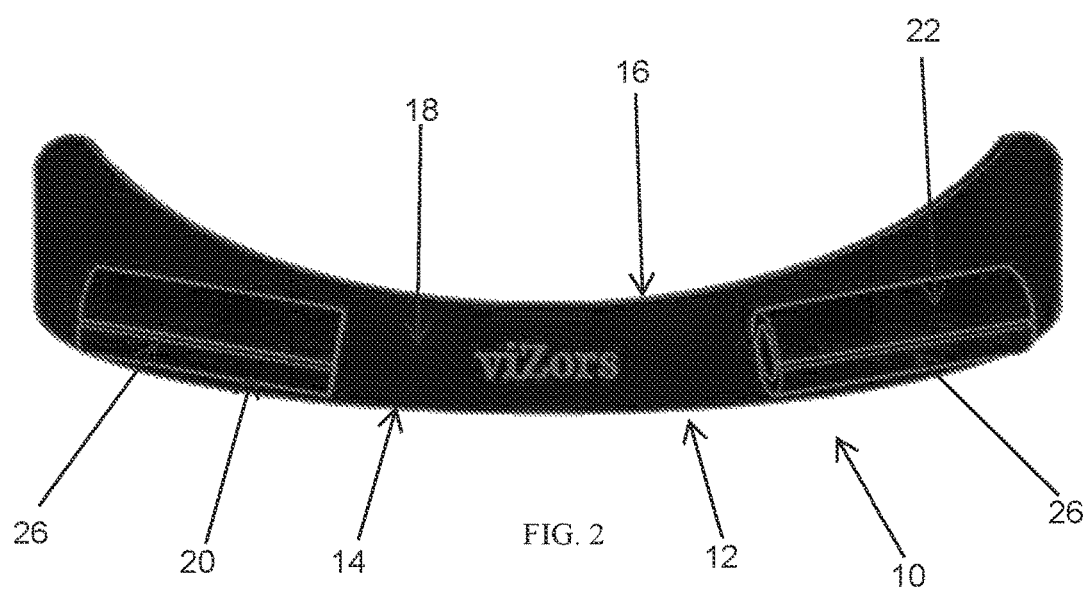
FIG. 2 is a bottom view of the illustrative embodiment of the protective shield of FIG. 1.

FIG. 2 illustrates a bottom view of the FIG. 1 protective shield (10). As illustrated, the protective shield (10) includes a body (12) including a front edge region (14), a rear edge region (16), a bottom surface (18) and a top surface (not shown). The body (12) is crescent-shaped and configured for attachment to eyewear (not shown) such that a portion of the body (12) provides a protective shield to the eyes of the wearer. The bottom surface (18) of the body (12) includes first (20) and second (22) attachment members for attaching to a top surface of eyewear (not shown). First (20) and second (22) attachment members extend from the bottom surface of the body (12) intermediate the front (14) and the rear (16) edge regions thereof. First (20) and second (22) attachment members comprise a hollow cylindrical body (not shown) with proximal and distal ends that define a longitudinal axis, wherein a slit (26) is positioned along a longitudinal portion of the periphery of the first (20) and second (22) attachment members and is configured to receive a top portion of eyewear (not shown).

Figure 3:
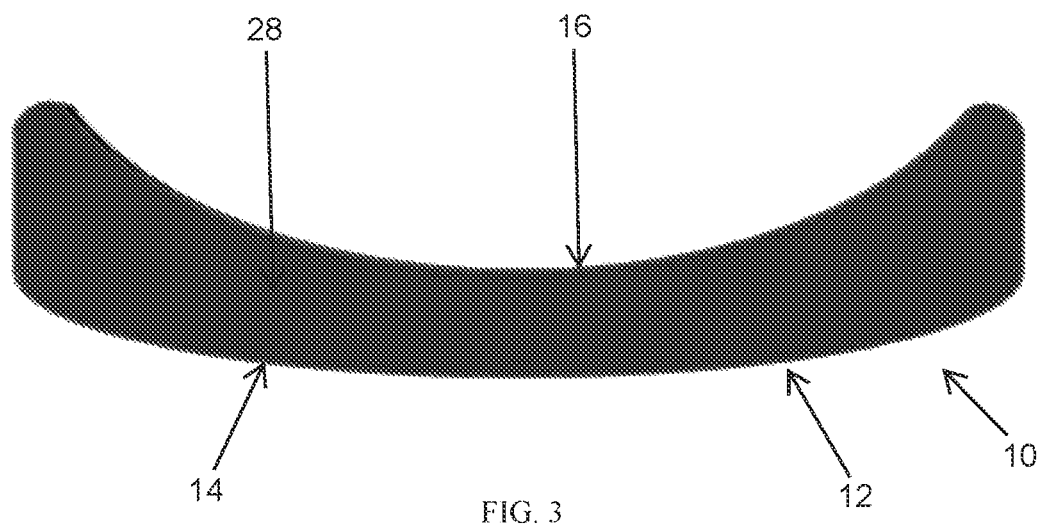
FIG. 3 is a top view of the illustrative embodiment of the protective shield of FIG. 1.

FIG. 3 illustrates a top view of the FIG. 1 protective shield (10). As illustrated, the protective shield (10) includes a body (12) including a front edge region (14), a rear edge region (16), a bottom surface (not shown) and a top surface (28). The body (12) is crescent-shaped and configured for attachment to eyewear (not shown) such that a portion of the body (12) provides a protective shield for the eyes of the wearer.

Figure 4:
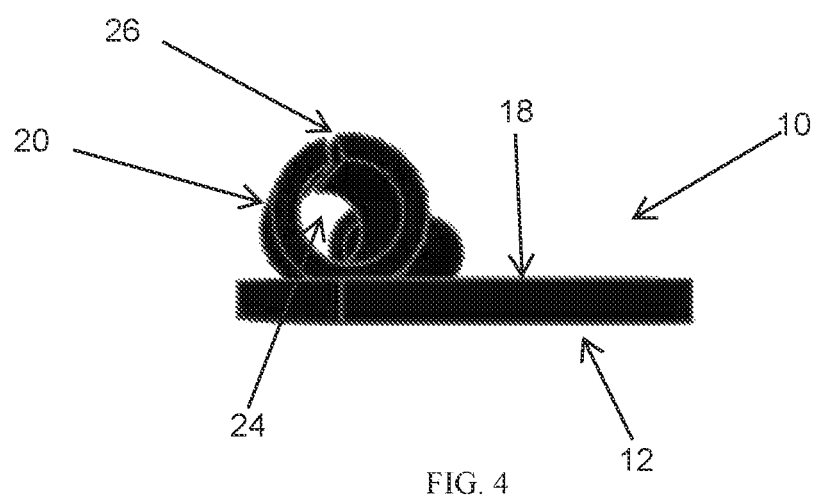
FIG. 4 is a right-side view of the illustrative embodiment of the protective shield of FIG. 1.

FIG. 4 illustrates a right-side view of the FIG. 1 protective shield (10). As illustrated, the protective shield (10) includes a body (12) including a bottom surface (18) and a top surface (28). The bottom surface (18) of the body (12) includes first (20) and second (not shown) attachment members for attaching to a portion of at least a portion of the top surface of the eyewear. First (20) and second (not shown) attachment members comprise a hollow cylindrical body (24) with opposite first and second ends that define a longitudinal axis, wherein a slit (26) is positioned along a longitudinal portion of the periphery of the first (20) and second (22) attachment members and is configured to receive a top portion of the eyewear (not shown).

Figure 5:
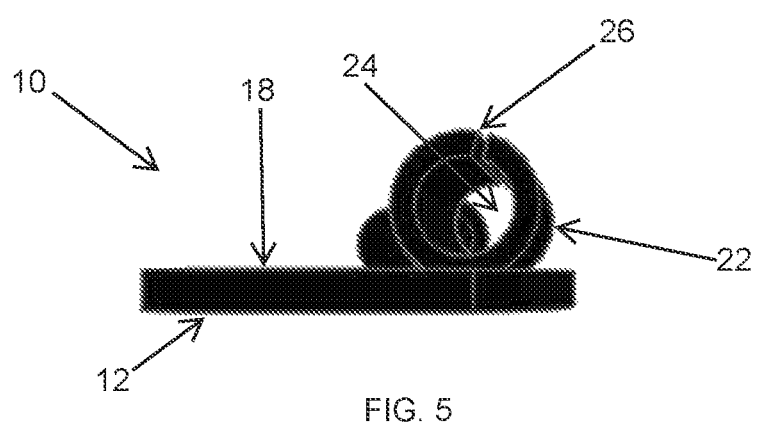
FIG. 5 is a left-side view of the illustrative embodiment of the protective shield of FIG. 1.

FIG. 5 illustrates a left-side view of the FIG. 1 protective shield (10). As illustrated, the protective shield (10) includes a body (12) including a bottom surface (18) and a top surface (28). The bottom surface (18) of the body (12) includes first (not shown) and second (22) attachment members for attaching to a portion of at least a portion of the top surface of the eyewear (not shown). First (not shown) and second (22) attachment members comprise a hollow cylindrical body (24) with opposite first and second ends that define a longitudinal axis, wherein a slit (26) is positioned along a longitudinal portion of the periphery of the first (not shown) and second (22) attachment members and is configured to receive a top portion of the eyewear (not shown).

Figure 6:
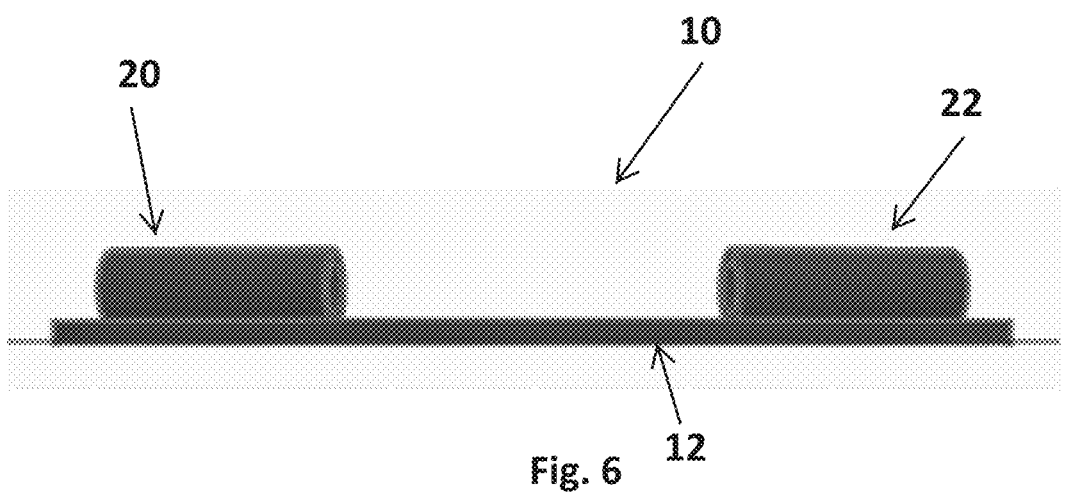
FIG. 6 is a front view of the illustrative embodiment of the protective shield of FIG. 1.

FIG. 6 illustrates a front view of the FIG. 1 protective shield (10). As illustrated, the protective shield (10) includes a body (12) including a bottom surface (18) and a top surface (28). The bottom surface (18) of the body (12) includes first (20) and second (22) attachment members for attaching to a portion of at least a portion of the top surface of the eyewear (not shown).

Figure 7:
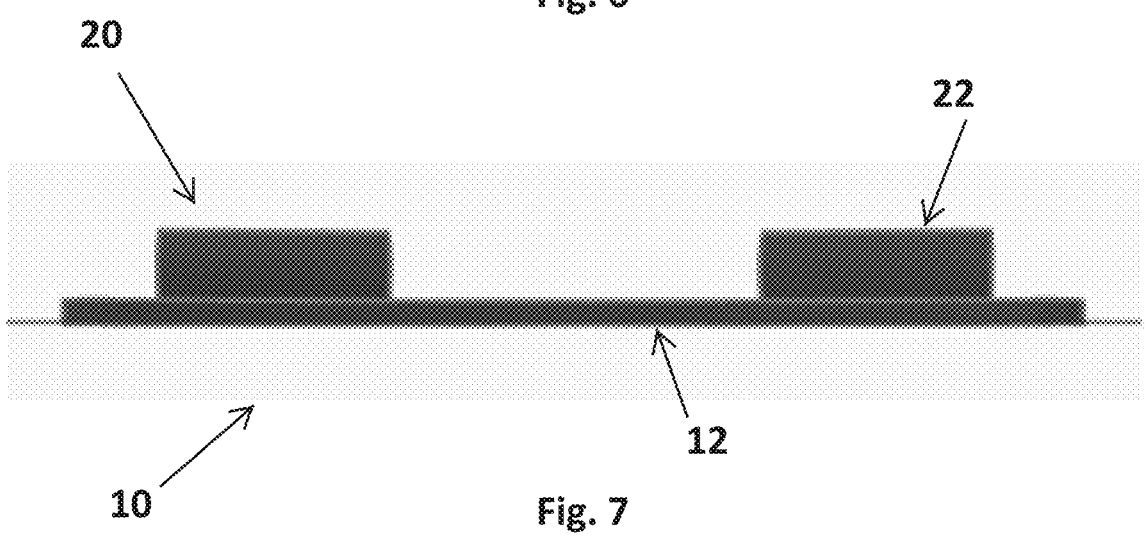
FIG. 7 is a rear view of the illustrative embodiment of the protective shield of FIG. 1.

FIG. 7 illustrates a rear view of the FIG. 1 protective shield (10). As illustrated, the protective shield (10) includes a body (12) including a bottom surface (18) and a top surface (28). The bottom surface of the body (12) includes first (20) and second (22) attachment members for attaching to a portion of at least a portion of the top surface of the eyewear (not shown).

Figure 8A:
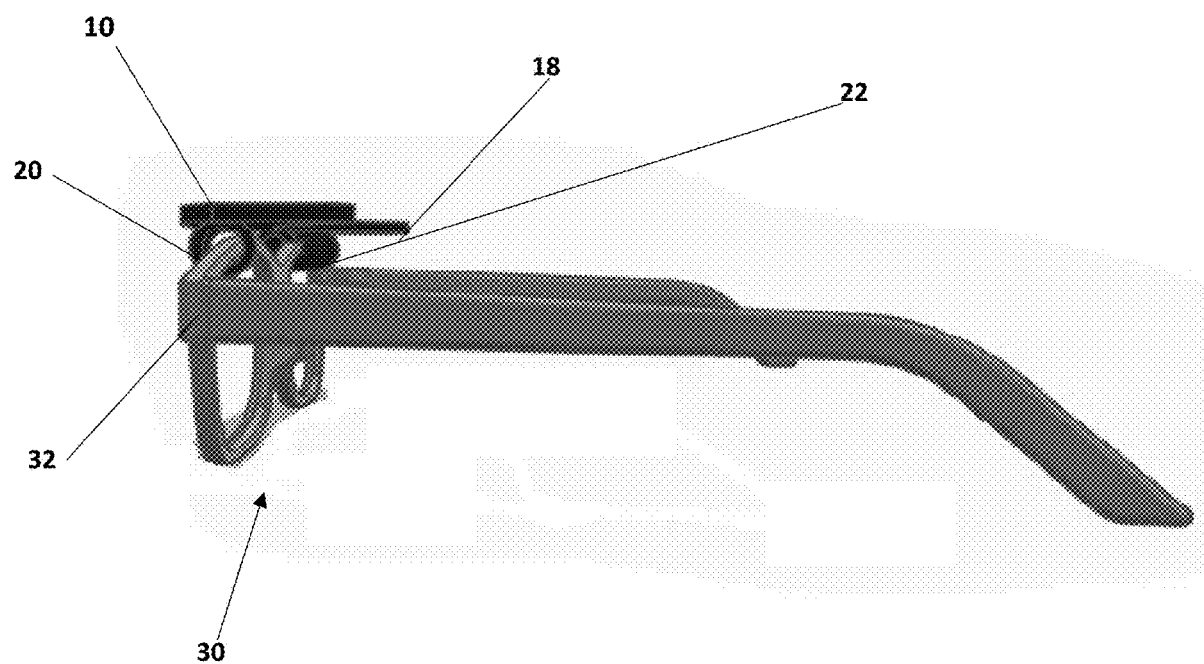
FIG. 8A is a side view an illustrative embodiment of the disclosed combination comprising the protective shield attached to the frame of eyewear.

FIG. 8A depicts a side view an illustrative embodiment of the disclosed combination comprising the protective shield attached to the frame of eyewear. FIG. 8A shows the combination of the protective shield (10) and eyewear (30) having a frame (32). According to the embodiment shown in FIG. 8A, the protective shield (10) is attached to the frame (32) of the eyewear (30). The protective shield (10) is attached to the frame (32) of the eyewear (30) through first (20) and second (22) attachment members that extend from the bottom major surface (18) of the protective shield.

Figure 8B:
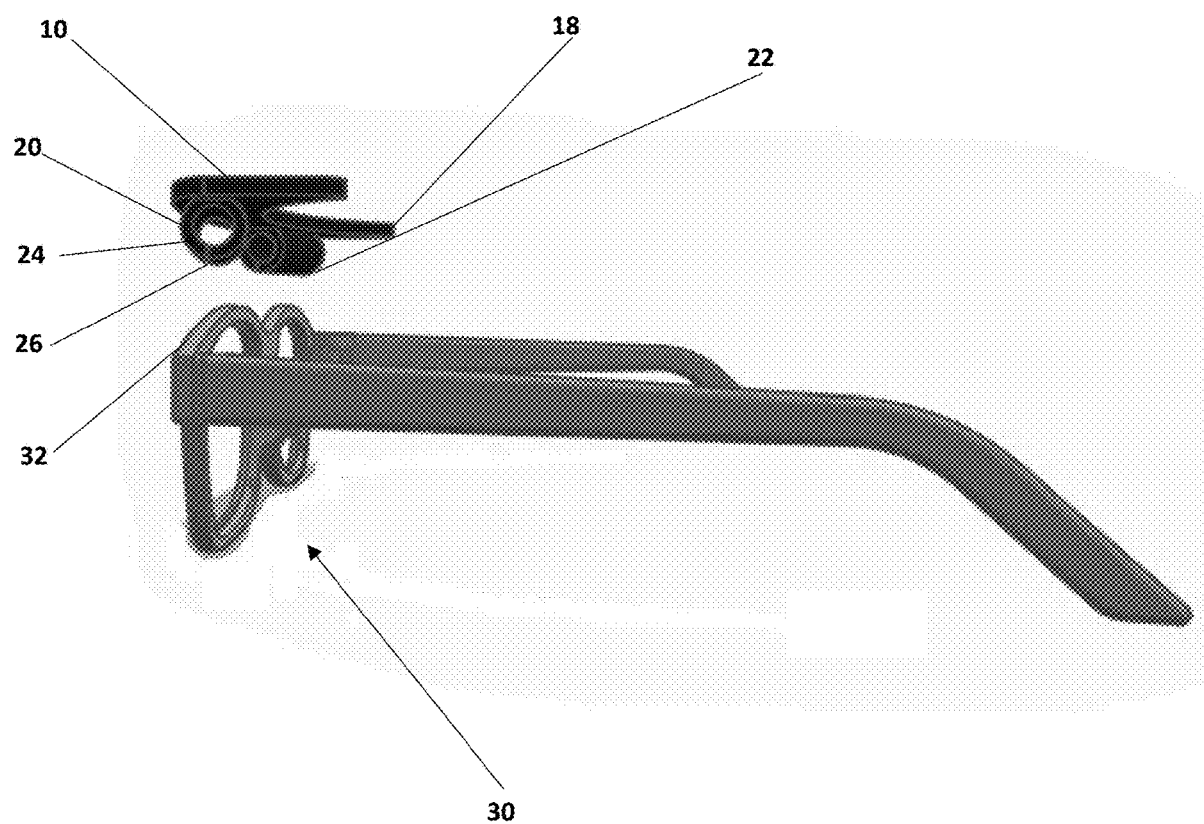
FIG. 8B is an exploded side view an illustrative embodiment of the disclosed combination comprising the protective shield in relation to the frame of eyewear.

FIG. 8B is an exploded side view an illustrative embodiment of the disclosed combination comprising the protective shield in relation to the frame of eyewear. FIG. 8B shows the combination of the protective shield (10) and eyewear (30) having a frame (32). According to the embodiment shown in FIG. 8B, the protective shield (10) is configured to be attached to the frame (32) of the eyewear (30) through first (20) and second (22) attachment members that extend from the bottom major surface (18) of the protective shield. Each of the first (20) and second (22) attachment members comprises a hollow cylindrical body (24) having a slit (26) configured to receive a top portion of the frame (32) of the eyewear (30).

Figure 8C:
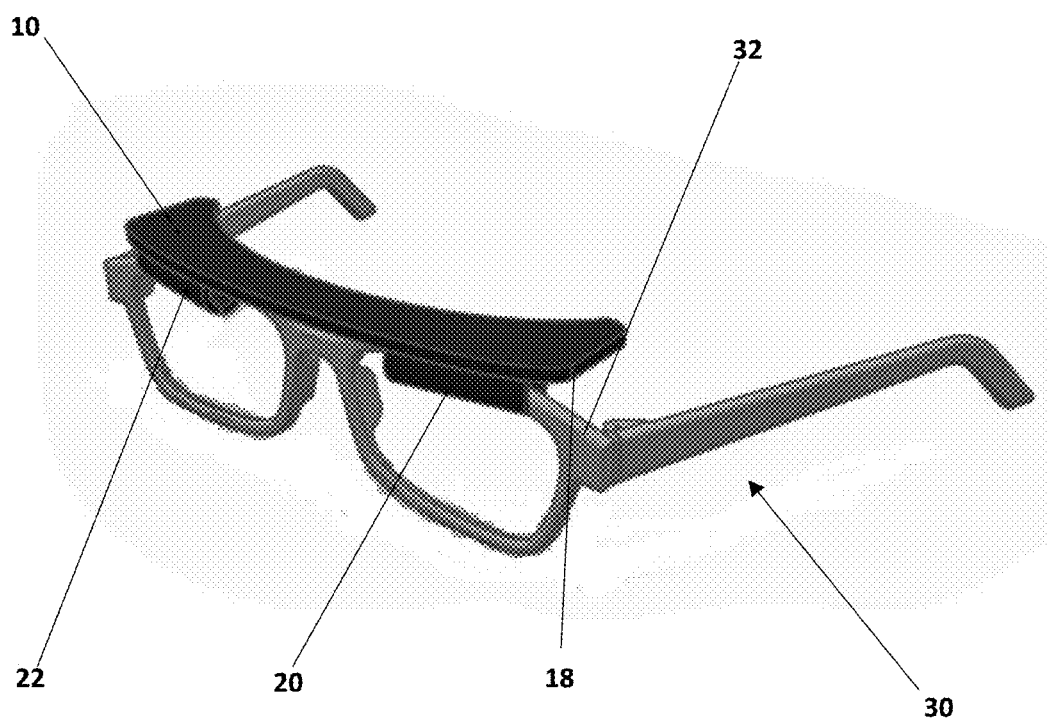
FIG. 8C is a front perspective view an illustrative embodiment of the disclosed combination comprising the protective shield attached to the frame of eyewear.

FIG. 8C is a front perspective view an illustrative embodiment of the disclosed combination comprising the protective shield attached to the frame of eyewear. FIG. 8C shows the combination of the protective shield (10) and eyewear (30) having a frame (32). According to the embodiment shown in FIG. 8C, the protective shield (10) is attached to the frame (32) of the eyewear (30). The protective shield (10) is attached to the frame (32) of the eyewear (30) through first (20) and second (22) attachment members that extend from the bottom major surface (18) of the protective shield.

Figure 8D:
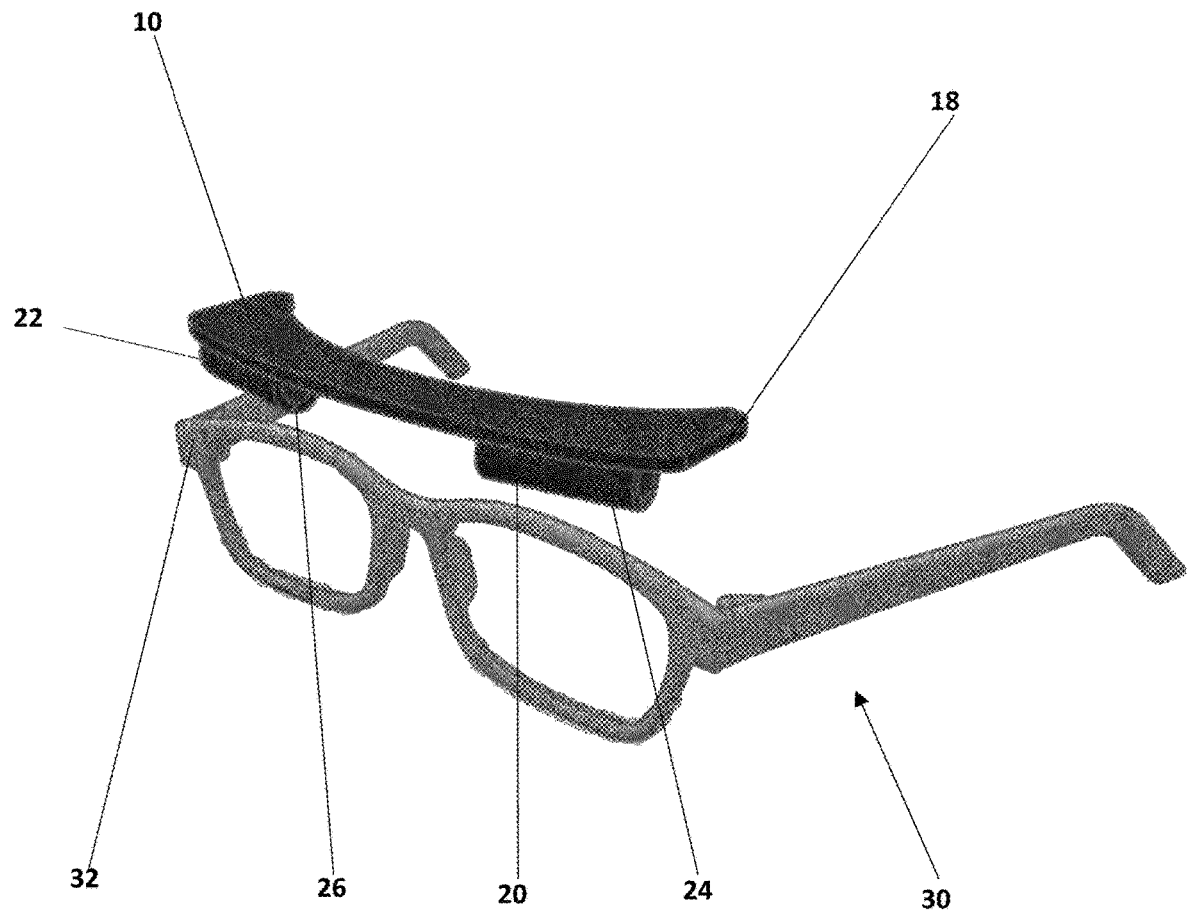
FIG. 8D is an exploded front perspective view an illustrative embodiment of the disclosed combination comprising the protective shield in relation to the frame of eyewear.

FIG. 8D is an exploded front perspective view an illustrative embodiment of the disclosed combination comprising the protective shield in relation to the frame of eyewear. FIG. 8D shows the combination of the protective shield (10) and eyewear (30) having a frame (32). According to the embodiment shown in FIG. 8D, the protective shield (10) is configured to be attached to the frame (32) of the eyewear (30) through first (20) and second (22) attachment members that extend from the bottom major surface (18) of the protective shield. Each of the first (20) and second (22) attachment members comprises a hollow cylindrical body (24) having a slit (26) configured to receive a top portion of the frame (32) of the eyewear (30).

It is to be understood that the exemplary embodiments are merely illustrative of the disclosure and that many variations of the above-described embodiments can be devised by one skilled in the art without departing from the scope of the disclosure. It is therefore intended that all such variations be included within the scope of the following claims and their equivalents.

The invention claimed is:

1. A protective shield for eyewear consisting essentially of:
    a body having opposite facing top and bottom major surfaces, a perimeter, a concave side surface to substantially conform to a wearer's forehead, and
    one or more resilient attachment members depending entirely from the bottom surface of the body and configured to removably attach the body to eyewear,
    wherein the attachment members include means for engaging the protective shield to the eyewear,
    wherein the attachment members comprise a hollow cylindrical body with proximal and distal ends that define a longitudinal axis, and wherein the means for engaging comprises a slit formed in the cylindrical body along at least a portion of the longitudinal axis of the hollow cylindrical body configured to receive a top portion of the eyewear.

2. The protective shield of claim 1, wherein said body is substantially planar.

3. The protective shield of claim 2, wherein the perimeter is defined by a front edge region, a rear edge region, and side edge regions, wherein said front edge region and said rear edge region are longer than said side edge regions.

4. The protective shield of claim 1, wherein said body is substantially opaque.

5. The protective shield of claim 1, wherein said body is substantially crescent-shaped.

6. The protective shield of claim 1, comprising at least two attachment members extending entirely from the bottom surface of the body of the protective shield.

7. The protective shield of claim 6, comprising only two attachment members extending entirely from the bottom surface of the body of the protective shield.

8. The protective shield of claim 6, wherein the at least two attachment members extend entirely from the bottom of the body intermediate the front edge region and the rear edge region.

9. The protective shield of claim 1, wherein the attachment members are integral with the bottom surface of the body of the protective shield.

10. The protective shield of claim 1, wherein the attachment members are removably attached to the bottom surface of the body of the protective shield.

11. A combination comprising:
    eyewear having a frame; and
    a protective shield removably attached to the frame of the eyewear, the protective shield comprising a body having opposite facing top and bottom major surfaces, a perimeter, a concave side surface to substantially conform to a wearer's forehead,
    one or more resilient attachment members depending entirely from the bottom surface of the body and configured to removably attach the body to eyewear,
    wherein the attachment members include means for engaging the protective shield to the eyewear formed in a portion of the body of the protective shield,
    wherein the attachment members comprise a hollow cylindrical body with proximal and distal ends that define a longitudinal axis, and wherein the means for engaging comprises a slit formed in the cylindrical body along at least a portion of the longitudinal axis of the hollow cylindrical body configured to receive a top portion of the eyewear.

12. The protective shield of claim 11, wherein the attachment members are not configured to permit the body to be removably attached directly to arms of the eyewear.

* * * * *